United States Patent [19]

Robinson et al.

[11] Patent Number: 4,469,814

[45] Date of Patent: Sep. 4, 1984

[54] CATALYSTS

[75] Inventors: Joseph G. Robinson, Winchcombe; David I. Barnes, Cheltenham, both of England

[73] Assignee: Coal Industry (Patents) Limited, London, England

[21] Appl. No.: 554,246

[22] Filed: Nov. 22, 1983

[30] Foreign Application Priority Data

Dec. 10, 1982 [GB] United Kingdom ................ 8235330

[51] Int. Cl.$^3$ .................. B01J 21/12; B01J 20/32; B01J 23/46; B01J 23/74

[52] U.S. Cl. .................. 502/263; 502/261; 502/258; 502/253; 502/244; 585/415

[58] Field of Search .............. 502/263, 261, 258, 253, 502/244; 585/415

[56] References Cited

U.S. PATENT DOCUMENTS

| | | | |
|---|---|---|---|
| 2,519,622 | 8/1950 | Archibald et al. | 502/263 |
| 3,457,192 | 7/1969 | Erickson et al. | 502/263 |
| 3,634,332 | 1/1972 | Bambrick | 502/263 |
| 3,652,216 | 3/1972 | Krekeler et al. | 502/330 |
| 3,969,274 | 7/1976 | Frampton | 502/258 |
| 4,427,578 | 1/1984 | Robinson et al. | 502/258 |

FOREIGN PATENT DOCUMENTS

| | | |
|---|---|---|
| 1028166 | 5/1966 | United Kingdom . |
| 1144494 | 3/1969 | United Kingdom . |
| 1161816 | 8/1969 | United Kingdom . |
| 1288638 | 9/1972 | United Kingdom . |
| 2097374 | 11/1982 | United Kingdom . |
| 2100710 | 1/1983 | United Kingdom . |

Primary Examiner—Delbert E. Gantz
Assistant Examiner—Chung K. Pak
Attorney, Agent, or Firm—Stevens, Davis, Miller & Mosher

[57] ABSTRACT

An improved catalyst for conversion of oxygen-containing aliphatics to hydrocarbons is a silica xerogel having a layer of an aluminum compound chemically bonded onto its surface, having a maximum pore diameter of 1.1 nm and having substantially only protons and/or transition metal cations as electrical charge balancing species. The catalyst is very specific for the production of aromatics.

11 Claims, No Drawings

CATALYSTS

This invention concerns improved catalysts, more particularly it concerns improved catalysts of a synthetic zeolite type.

Synthetic zeolite catalysts, such as those produced by Mobil under the designation ZSM-5, are known to convert methanol, synthesis gas and many oxygen-containing organis compounds into saturated and unsaturated lower hydrocarbons, offering the possibility of gasoline production. In our co-pending British Application No. 82/11371, Publication no. 2,100,710A, we have described a novel synthetic zeolite catalyst which comprises a highly porous amorphous silica xerogel having a layer of an amphoteric metal compound chemically bonded onto up to 90% of the available surface, the catalyst having a maximum pore diameter of about 1.5 nm. The metal is preferably aluminum, thereby giving a synthetic catalyst having an active aluminosilicate layer which may exist in one or two major crystal planes. It is now thought that the aluminosilicate layer has free aluminum-derived cations associated therewith and that cationic species such as $Al(OH)_2+$ may balance negatively charged 4- co-ordinate aluminum bonded to the surface of the silica xerogel. This and other explanations contained herein are to be regarded as theoretical only and have no bearing on the scope of the present invention.

The present invention provides a synthetic catalyst which comprises a highly porous amorphous silica xerogel having a layer of an aluminum compound chemically bonded onto the silica surface, in an amount equivalent to a monolayer on up to 90% of the BET surface area of the silica, the catalyst having a maximum pore diameter of about 1.1 nm and having substantially only protons and/or transition metal cations as electrical charge balancing species on the surface of the layer, the reaction causing bonding of the layer having been carried out at a temperature of from 300° to 1200° C. and the catalyst having been calcined at a temperature not exceeding 1200° C.

The present invention provides a process for the production of synthetic catalysts comprising the steps of:

(a) treating a dry highly porous amorphous silica xerogel with an anhydrous hydrolysable compound of aluminum in an amount sufficient to cover up to 90% of the BET surface area of the silica with a monolayer of the compound and removing the solvent;

(b) causing the surface of the silica to react with the compound by heating to a temperature of from 300° to 1200° C. to yield a material having a maximum pore diameter of about 1.1 nm, and (c) treating the product material of step (b) with an ammonium salt solution capable of exchanging labile cations for ammonium ions, washing the treated material with deionised water until no further ammonium cations can be detected, optionally ion exchanging to deposit transition metal cations on the surface, drying and calcining the material at a temperature not exceeding 1200° C. to yield the catalyst.

Steps (a) and (b) of the process are preferably carried out by a method derived from British Published Application No. 2,100,710A, by treating the highly porous amorphous silica xerogel, having a suitable porosity, with a solution of the predetermined quantity of the hydrolysable compound of aluminum, removing the solvent to leave a layer of the compound on up to 90% of the available surface area, and causing the surface of the silica to react with the layer to chemically bond the aluminum to the surface of the silica. We have found that the temperature of reaction in process step (b) can affect the catalytic properties of the product catalyst. Preferably the reaction temperature is 400° to 900° C., more preferably 450° to 550° C. The reaction is preferably affected by heating at the appropriate temperature for some hours. Preferred catalysts have a deposition of aluminum compound equivalent to about 50% coverage of the BET surface.

Preferably, the silica xerogel having the deposited layer is treated in step (c) with a dilute aqueous solution of an ammonium salt such as ammonium nitrate. The material is conveniently treated packed in a column, through which the solution may be passed until analysis demonstrates that no further aluminum cations are found in the eluent. The solution is then displaced by deionised water, which is passed until no further trace of ammonium ion is detected; this is conveniently done by comparing the pH of the eluent with that of the deionised water feed. These treatments are conveniently done under ambient conditions of temperature and pressure, but may also be carried out below or above ambient.

An ion-exchange step may be incorporated. Such ion-exchange steps have been described in the literature and can be carried out in manner known per se, suitably using a salt such as a nitrate. Preferred metals are lanthanum and rhodium.

After washing, the catalyst material is dried, conveniently under reduced pressure, and then calcined, preferably at a temperature of 300°–900° C., more preferably 450°–600° C. and suitably for 4 to 10 hours.

The catalyst of the invention is especially useful in the conversion of oxygen-containing aliphatics to hydrocarbons and water, such organics being preferably selected from alcohols and ethers and especially methanol. The catalyst may also be used, along or in combination with, that is admixed with or directly subsequent to, a second catalyst, for the direct conversion of synthesis gas. Such a second catalyst may be a Fischer-Tropsch type catalyst such as a transition metal, for example, iron, catalyst. Alternatively the synthesis gas may be converted to methanol using a catalyst carrier impregnated with zinc and chromium or zinc and copper, or impregnated with a noble metal such as ruthenium. For the conversion of methanol, the catalyst may be used in a conventional reactor, using fixed, moving or fluidised beds. Temperatures are preferably in the range 300° to 500° C., especially 350° to 450° C. The Liquid Hourly Space Velocity (LHSV) is preferably from 0.1 to 1 $h^{-1}$, more preferably 0.2 to 0.5 $h^{-1}$. Under preferred conditions, the catalyst gives high conversion yields, approaching 100% per pass, and demonstrates an unusual and very high selectivity towards aromatics. This selectivity is materially and unexpectedly different from that observed using the untreated starting material catalyst, from that using the Na-form of the catalyst and from that found using Mobil's ZSM-5 catalyst.

Thus, the invention also provides a process for the conversion of an oxygen-containing aliphatic compound into hydrocarbons, comprising passing the compound in vapour form, over the catalyst at a temperature of 250° to 500° C. and at a LHSV of 0.1 to 1 $h^{-1}$. The optimum reaction temperature of step (b) and the calcination temperature of step (c) are thought to be about 500° C. and 550° C., respectively, for a catalyst for the conversion of oxygen-containing aliphatic compounds into hydrocarbons.

The preparation of catalysts according to the invention and their use in a conversion process will now be described by way of example only.

EXAMPLE

A sample (100 g) of commercial silica xerogel was heated in an oven for 4 hours at 120° C. to remove physically absorbed water. The dried xerogel was cooled in a desiccator and immersed in 250 ml of a 33.87% w/v solution of aluminum sec-butoxide in dry hexane (an amount sufficient to cover 50% of the BET surface with a monolayer of the aluminum alkoxide after removal of the solvent) and the pressure reduced to allow liquid to enter the pores of the xerogel. After 12 hours, excess solution was decanted and the material transferred to a vacuum oven where it was dried. After soaking in deionised water for 16 hours to complete hydrolysis of the alkoxide and decanting the liquor the material was dried in the vacuum oven. The material was heated at 500° C. for 4 hours, to complete reaction of the aluminum compound with the surface of the xerogel. This was designated "Catalyst A".

A sample of Catalyst A was packed into a column and a 0.1M aqueous solution of ammonium nitrate was pumped through the column. Samples of the eluent were tested periodically for the presence of aluminum by the addition of a few drops of 0.1M sodium hydroxide solution; samples containing aluminum cation were characterised by the formation of a gelatinous precipitate. When no further aluminum could be detected in this way, the ammonium nitrate solution was replaced by deionised water and pumping continued until the pH of the eluent was identical with that of the feed water. The product was removed from the column, dried under reduced pressure and thereafter calcined at 500° C. for 6 hours. This was designated "Catalyst B".

High resolution electron microscopy of Catalyst B showed that it was composed of particles of 2–10 nm diameter having a strongly electron scattering surface layer which was an integral part of the silica matrix. There was little fine microporosity but the gaps between the particles were approximately 1.0 nm.

Degassed methanol was pumped by a positive displacement pump through a preheater packed with glass beads before the methanol vapour was passed into a tubular reactor packed with the catalyst on test. The tubular reactor was run at various temperatures, 300°, 350°, 400° and 450° C., and the preheater was maintained at 5° C. below the reaction temperature. The products emerging from the reaction tube were collected as a liquid fraction in an ice-cooled trap and a gaseous fraction in a gas reservoir. The products were analysed and the results are shown in the Table below.

It will be observed from the results that using Catalyst B, according to the invention, especially at a LHSV of 0.3 hr$^{-1}$ a very high specificity for aromatics is demonstrated.

Similar tests were performed using a form of Catalyst B that had been calcined at 325° C., and a conversion of methanol to hydrocarbons of 19.1% was obtained at a bed temperature of 350° C. A form of Catalyst B, but calcined at 700° C., converted methanol to hydrocarbons in a yield of 69% at a bed temperature of 350° C., with high selectivity to aromatics.

The Na-form of Catalyst A, that is Catalyst A ion-exchange with sodium, was tested in the same apparatus and at a bed temperature of 450° C. at a LHSV of 0.1 h$^{-1}$. A conversion of less than 3% was observed; no aromatic hydrocarbons were detected in the products.

TABLE

| Catalyst | ZSM-5[a] | Catalyst A | | Catalyst B | | | |
|---|---|---|---|---|---|---|---|
| LHSV (h$^{-1}$) | 1.0 | 0.3 | 0.3 | 0.3 | 0.3 | 1.0 | 1.0 |
| Temperature (°C.) | 370 | 350 | 450 | 350 | 450 | 350 | 450 |
| Conversion (wt %) | 100 | 85 | 95 | 99.8 | 98.7 | 39.0 | 64.4 |
| Product distribution (wt %) | | | | | | | |
| Methanol | 1.0 | 2.40 | 11.20 | 0.03 | 7.70 | 3.70 | 8.60 |
| Ethane | 0.6 | 9.10 | 16.90 | 0.50 | 3.20 | 0.20 | 0.90 |
| Propane | 16.2 | 6.20 | 7.20 | 0.01 | 1.30 | 0.10 | 1.80 |
| Butanes | 24.3 | 2.80 | 9.40 | 1.05 | 0.02 | 0.05 | 1.90 |
| Pentanes | 9.1 | 1.10 | 3.00 | 0.02 | 0.02 | — | 0.10 |
| C$_5^+$ Alkanes | 4.3 | 4.40 | 7.50 | 0.12 | 0.03 | 0.10 | 0.02 |
| Ethene | 0.5 | 7.60 | 10.40 | 0.01 | 5.00 | 0.10 | 1.20 |
| Propene | 1.0 | 3.90 | 4.30 | 0.40 | 0.20 | — | 0.10 |
| But-1-ene | 1.3 | — | — | 0.20 | 0.10 | — | — |
| Hexene | — | — | — | 0.02 | — | — | 0.10 |
| Benzene | 1.7 | — | — | — | — | — | — |
| C$_7$ Alkylbenzene | 10.5 | 5.80 | 7.00 | 7.20 | 3.70 | 2.90 | 2.70 |
| C$_8$ Alkylbenzene | 18.0 | 8.90 | 5.10 | 5.40 | 4.70 | 1.10 | 2.70 |
| C$_9$ Alkylbenzene | 7.5 | 3.20 | 5.90 | 2.30 | 8.60 | 1.30 | 2.00 |
| C$_{10}$ Alkylbenzene | 3.3 | 10.80 | 1.50 | 31.30 | 27.60 | 2.10 | 3.80 |
| C$_{11}$ Alkylbenzene | 0.2 | 9.70 | 0.60 | 9.00 | 7.10 | 0.80 | 1.80 |
| C$_{12}$ Alkylbenzene | — | 9.90 | 0.60 | 15.00 | 6.40 | 1.50 | 0.80 |
| C$_{13}$ Alkylbenzene | — | 13.90 | 8.90 | 25.40 | 20.10 | 2.90 | 2.00 |
| % Aromatics | 41.5 | 62.9 | 28.6 | 97.6 | 81.4 | 73 | 52 |

NOTE:
[a]Results published in J. Catal. 1977, 47. 249

We claim:

1. A process for the production of synthetic catalysts comprising the steps of:
    (a) treating a dry highly porous amorphous silica xerogel with an anhydrous hydrolysable compound of aluminum in an amount sufficient to cover up to 90% of the BET surface area of the silica with a monolayer of the compound and removing the solvent;
    (b) causing the surface of the silica to react with the compound by heating to a temperature of from 300° C. to 1200° C. to yield a material having a maximum pore diameter of about 1.1 nm, and (c) treating the product material of step (b) with an ammonium salt solution capable of exchanging labile cations for ammonium ions, washing the treated material with deionised water until no further ammonium cations can be detached.

2. The process as claimed in claim 1, further comprising depositing transition metal cations on the surface of the treated material by ion exchanging, drying and calcining the ion exchanged material by subjecting it to a temperature not exceeding 1200° C.

3. A process as claimed in claim 1, wherein the amount of aluminum compound in step (a) is sufficient to cover approximately 50% of the BET surface area of the silica.

4. A process as claimed in claim 1, wherein the reaction temperature of step (b) is from 400° to 900° C.

5. A process claimed in claim 4, wherein the reaction temperature is 450° to 550° C.

6. A process as claimed in claim 1, wherein the calcining temperature of step (c) is from 300° to 900° C.

7. A process as claimed in claim 6, wherein the calcining temperature is from 450° to 600° C.

8. A synthetic catalyst comprising a highly porous amorphous silica xerogel having a layer of an aluminum compound in an amount equivalent to a monolayer covering up to 90% of the BET surface area of the silica, chemically bonded onto the surface thereof, said catalyst having a maximum pore diameter of about 1.1 nm and having substantially only protons and/or transition metal cations as electrical charge balancing species on the surface of the layer, the reaction causing bonding of the layer having been carried out at a temperature from 300° to 1200° C.

9. A catalyst as claimed in claim 8, wherein the layer of aluminum compound is equivalent to a monolayer on about 50% of the BET surface area of the silica.

10. A catalyst as claimed in claim 8, wherein the reaction temperature was 400° to 900° C.

11. A catalyst as claimed in claim 8, wherein the calcination temperature was 300° to 900° C.

* * * * *